United States Patent
Ivanov et al.

(10) Patent No.: US 8,208,136 B2
(45) Date of Patent: Jun. 26, 2012

(54) LARGE AREA SUBSTRATE FOR SURFACE ENHANCED RAMAN SPECTROSCOPY (SERS) USING GLASS-DRAWING TECHNIQUE

(75) Inventors: Ilia N. Ivanov, Knoxville, TN (US); John T. Simpson, Clinton, TN (US)

(73) Assignee: UT-Battelle, LLC, Washington, DC (US)

(*) Notice: Subject to any disclaimer, the term of this patent is extended or adjusted under 35 U.S.C. 154(b) by 421 days.

(21) Appl. No.: 12/558,145

(22) Filed: Sep. 11, 2009

(65) Prior Publication Data
US 2011/0063610 A1    Mar. 17, 2011

(51) Int. Cl.
*G01J 3/44* (2006.01)
(52) U.S. Cl. ...................................................... 356/301
(58) Field of Classification Search .................. 356/301
See application file for complete search history.

(56) References Cited

U.S. PATENT DOCUMENTS

| | | | |
|---|---|---|---|
| 3,953,131 A | 4/1976 | Britz | 356/141 |
| 4,912,314 A * | 3/1990 | Sink | 250/207 |
| 5,110,334 A | 5/1992 | Ayers | 65/2 |
| 5,400,136 A | 3/1995 | Vo-Dinh | |
| 6,532,326 B1 | 3/2003 | Hutchinson et al. | |
| 6,552,842 B2 | 4/2003 | Simpson et al. | |
| 6,661,952 B2 | 12/2003 | Simpson et al. | |
| 6,757,463 B2 | 6/2004 | Hutchinson et al. | |
| 6,853,669 B2 | 2/2005 | Simpson et al. | |
| 7,139,072 B1 | 11/2006 | Boss et al. | |
| 7,150,904 B2 | 12/2006 | D'Urso et al. | |
| 7,258,731 B2 | 8/2007 | D'Urso et al. | |
| 7,267,948 B2 | 9/2007 | Vo-Dinh | |
| 7,312,088 B2 | 12/2007 | Farquharson | |
| 7,312,875 B2 | 12/2007 | Hanson et al. | |
| 7,351,588 B2 | 4/2008 | Poponin | |
| 7,767,564 B2 | 8/2010 | Dutta | 438/585 |
| 2002/0121856 A1 | 9/2002 | Tsai | |
| 2005/0109918 A1 | 5/2005 | Nikzad et al. | |
| 2005/0196775 A1 | 9/2005 | Swager et al. | 435/6 |
| 2005/0264157 A1 | 12/2005 | Sakai et al. | 136/255 |
| 2006/0017917 A1 * | 1/2006 | Cullum et al. | 356/301 |
| 2006/0023451 A1 | 2/2006 | Han et al. | 362/249 |
| 2006/0034729 A1 | 2/2006 | Poponin | |
| 2006/0252065 A1 | 11/2006 | Zhao et al. | |
| 2006/0279191 A1 | 12/2006 | Geohegan et al. | |
| 2006/0289380 A1 | 12/2006 | D'Urso et al. | |
| 2007/0048249 A1 | 3/2007 | Youngblood et al. | |

(Continued)

OTHER PUBLICATIONS

Xuejun Zhang et al., "*Mass-Productions of vertically Aligned Extremely Long Metallic Micro/Nanowires Using Fiber Drawing Nanomanufacturing*", Advanced Materials, 2008, pp. 105.

(Continued)

*Primary Examiner* — Kara E Geisel
(74) *Attorney, Agent, or Firm* — Brinks Hofer Gilson & Lione

(57) ABSTRACT

A method of making a large area substrate comprises drawing a plurality of tubes to form a plurality of drawn tubes, and cutting the plurality of drawn tubes into cut drawn tubes. Each cut drawn tube has a first end and a second end along the longitudinal direction of the respective cut drawn tube. The cut drawn tubes collectively have a predetermined periodicity. The method of making a large area substrate also comprises forming a metal layer on the first ends of the cut drawn tubes to provide a large area substrate.

20 Claims, 11 Drawing Sheets

U.S. PATENT DOCUMENTS

| | | |
|---|---|---|
| 2007/0131266 A1 | 6/2007 | Dutta |
| 2007/0155021 A1 | 7/2007 | Zhang et al. |
| 2007/0164270 A1 | 7/2007 | Majumdar et al. .............. 257/14 |
| 2008/0026188 A1 | 1/2008 | D'Urso et al. |
| 2008/0061689 A1 | 3/2008 | Ohkubo et al. |
| 2008/0080816 A1 | 4/2008 | D'Urso et al. |
| 2008/0144026 A1 | 6/2008 | Zhao et al. |
| 2008/0160865 A1 | 7/2008 | Wei et al. |
| 2008/0169016 A1 | 7/2008 | Dutta ........................... 136/238 |
| 2008/0191606 A1 | 8/2008 | Geohegan et al. |
| 2008/0198376 A1 | 8/2008 | Poponin |
| 2008/0296252 A1 | 12/2008 | D'Urso et al. |
| 2009/0042469 A1 | 2/2009 | Simpson |

OTHER PUBLICATIONS

Andris V. Bune et al., "*Materials Research in Low Gravity*", SPIE—The International Society for Optical Engineering, vol. 3123, 1997, 12 pgs.

Reinhold J. Dorn et al. "*Design of the Crires 512 X4096 Pixels Aladdin InSb Focal Plane Array Detector Mosaic*", European Southern Observatory, 4 pgs.

Zhihua Xu et al., "*Carbon nanotube effects on electroluminescence and photovoltaic response in conjugated polymers*", Applied Physics Letters 87, 263118 (2005), 3pgs.

Yu. A. Goldberg, "*Handbook Series on Semiconductor Parameters*", vol. 1, M. Levinshtein, S. Rumyantsev and M. Shur, ed, World Scientific, London, 1996, pp. 191-213.

Yue Wang et al. "*Growth and properties of 40 mm diameter Hg1-xCdxTe using the two-stage Pressurized Bridgman Method*", Journal of Crystal Growth, vol. 273, Issues 1-2, Dec. 17, 2004, pp. 54-62.

Yue Wang et al., "*A two-stage technique for single crystal growth of HgCdTe using a pressurized Bridgman method*", Journal of Crystal Growth, vol. 263, Issues 1-4, Mar. 1, 2004, pp. 273-282.

A. Rogalski, "*HgCdTe infrared detector material: history, status and outlook*", Institute of Physics Publishing, Reports on Progress in Physics, vol. 68, 2005, pp. 2267-2336.

D. F. Gibbons, "*Thermal Expansion of Some Crystals with the Diamond Structure*", Physical Review, vol. 112, No. 1,, Oct. 1, 1958, pp. 136-140.

\* cited by examiner

LARGE AREA SUBSTRATE FOR SURFACE ENHANCED RAMAN SPECTROSCOPY (SERS) USING GLASS-DRAWING TECHNIQUE

This invention was made with government support awarded by the U.S. Department of Energy (Prime Contract No. DE-AC05-00OR22725). The government has certain rights in the invention.

The present disclosure is related to U.S. patent application Ser. No. 12/588,129 to Ivanov et al., filed on the same date as this disclosure, entitled "Method For Morphological Control And Encapsulation Of Materials For Electronics And Energy Applications" and commonly owned by the assignee of the present disclosure, the entirety of which is hereby incorporated by reference. The present disclosure is also related to U.S. patent application Ser. No. 12/558,101 to Ivanov et al., filed on the same date as this disclosure, entitled "Method Of Making Large Area Conformable Shape Structures For Detector/Sensor Applications Using Glass Drawing Technique And Post processing" and commonly owned by the assignee of the present disclosure, the entirety of which is hereby incorporated by reference.

TECHNICAL FIELD

The present disclosure relates to a method of making large area substrates for surface enhanced Raman spectroscopy (SERS) using a glass-drawing technique, and a large area substrate prepared by same.

BACKGROUND

Surface enhanced Raman spectroscopy, or surface enhanced Raman scattering, is a surface sensitive technique that results in the enhancement of Raman scattering by molecules adsorbed on rough metal surfaces. The enhancement factor can be in a range of many orders of magnitude, which allows the technique to be sensitive enough to detect single molecules.

BRIEF SUMMARY

In one aspect, a method of making a large area substrate comprises drawing a plurality of tubes to form a plurality of drawn tubes, and cutting the plurality of drawn tubes into cut drawn tubes. Each cut drawn tube has a first end and a second end along the longitudinal direction of the respective cut drawn tube. The cut drawn tubes collectively have a predetermined periodicity. The method of making a large area substrate also comprises forming a metal layer on the first ends of the cut drawn tubes to provide a large area substrate.

In another aspect, a large area substrate comprises a plurality of bundled drawn tubes each having a first end and a second end along the longitudinal direction of the bundled drawn tubes. The bundled drawn tubes collectively have a predetermined periodicity. The first ends of the plurality of bundled drawn tubes have a plurality of protrusive surface features. The large area substrate also comprises a metal layer disposed on the plurality of protrusive surface features.

In yet another aspect, a method for detecting an analyte comprises providing a large area substrate comprising a plurality of bundled drawn tubes each having a first end and a second end along the longitudinal direction of the bundled drawn tubes. The bundled drawn tubes collectively have a predetermined periodicity. The first ends of the plurality of bundled drawn tubes have a plurality of protrusive surface features and a metal layer is disposed on the plurality of protrusive surface features. The method for detecting an analyte also comprises contacting the large area substrate with an analyte, and analyzing for the presence of the analyte.

DETAILED DESCRIPTION OF THE PREFERRED EMBODIMENTS

Figure 1:
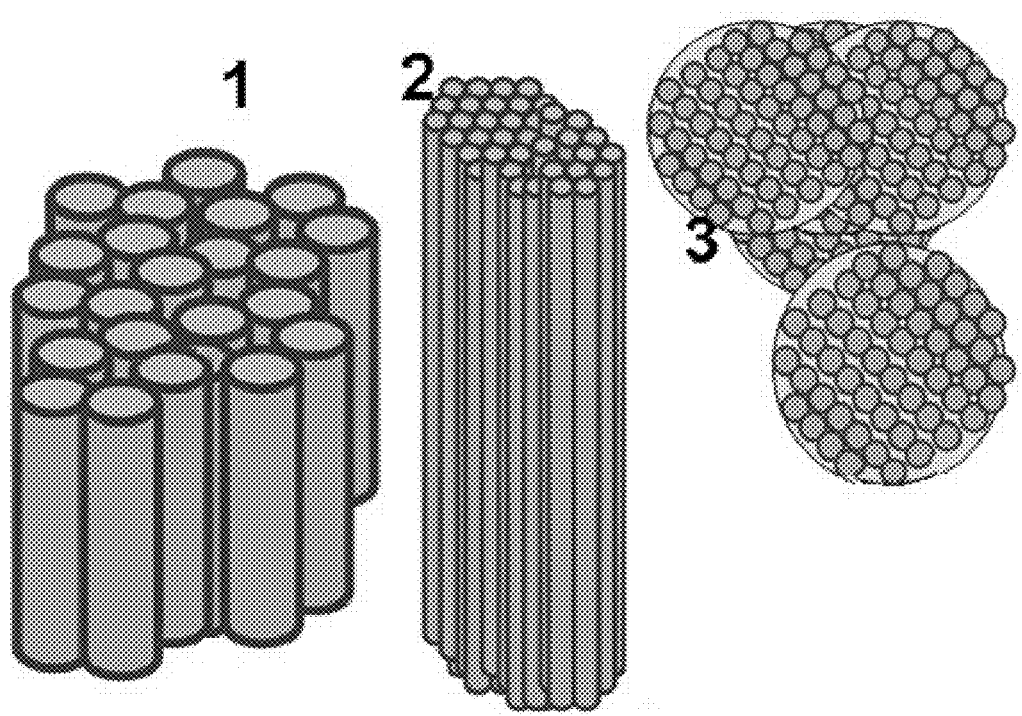
FIG. 1 is a not-to-scale schematic view of the method of making large area substrates for surface enhanced Raman spectroscopy.

The present disclosure is directed to a method of making large area substrates for surface enhanced Raman spectroscopy (SERS) using a glass-drawing technique, and a large area substrate prepared by same. The large area substrates prepared according to various embodiments of the present disclosure, however, can be used in any suitable applications, such as analytical instrumentation, analytical chemistry, and spectroscopy. Preferably, the large area substrates are used for SERS.

SERS is a form of Raman spectroscopy which involves the study of samples adsorbed to or interacting in some manner with metal surfaces of SERS substrates, typically nanoscale featured gold or silver surfaces, or, gold or silver colloids. Under the appropriate conditions, SERS may give rise to spectral enhancements of several orders of magnitude compared to normal Raman scattering.

One factor that affects sensitivity of SERS is surface roughness. Surface roughness can be an increased surface area relative to an otherwise planar surface, such as regions with a plurality of surface features, such as protrusions, bumps, pits, nanoparticles, and the like. In one example, a surface including colloidal silver with an average particle diameter of 40 nm is considered rough, although each colloidal particle is substantially smooth. Other examples of SERS active surfaces include, but are not limited to, metal substrates, lithographic assemblies, and vapor deposited surfaces.

In SERS applications, if the scattering surfaces of the substrates are periodic in nature, the Raman enhancement is even greater and will allow even easier detection of specific molecules. The sensitivity to specific molecules using a periodic array is determined by the size, shape, and periodicity of the surface features.

A variety of methods can be used to prepare SERS substrates. In one example, isolated metal nanosphere particles, metal spheroid particles, or metal coated dielectric nanoparticles are integrated onto a base support substrate. The particles may be disposed on the substrate to form a random nanostructure or a regular nanostructure. The regular nanostructure may be prepared using lithographic techniques. In another example, the SERS substrates are preferably prepared by a glass drawing technique.

Large Area Substrates For Surface Enhanced Raman Spectroscopy (SERS)

Roughness and periodicity of SERS substrates may further increase the SERS enhancement. The glass drawing technique can be used to prepare structured substrates that may have various periodicities and shapes. The periodicity of the structured substrates can be determined by the periodicity of the bundled tubes before cutting. The structured substrates can comprise tubes with protrusive features such as spikes, recesses, and cones, hollow tubes, or filled tubes. These tubes may be in nanoscale in diameter, and thus may be referred to as "nanotubes". These protrusive features may have a predetermined periodicity. The structured substrates can be super-hydrophobic or super-hydrophilic. The structured substrates can also be coated with a metal.

Figure 2A:
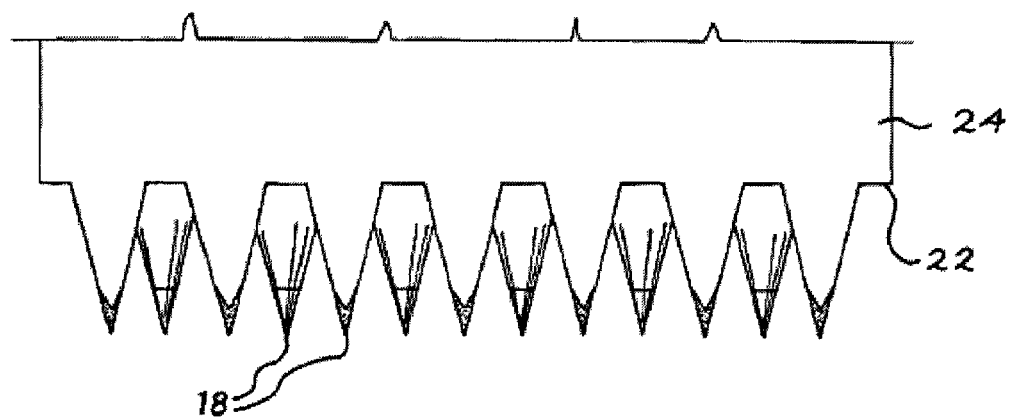
FIG. 2 is a not-to-scale schematic view of a large area substrate for surface enhanced Raman spectroscopy.
Figure 2B:
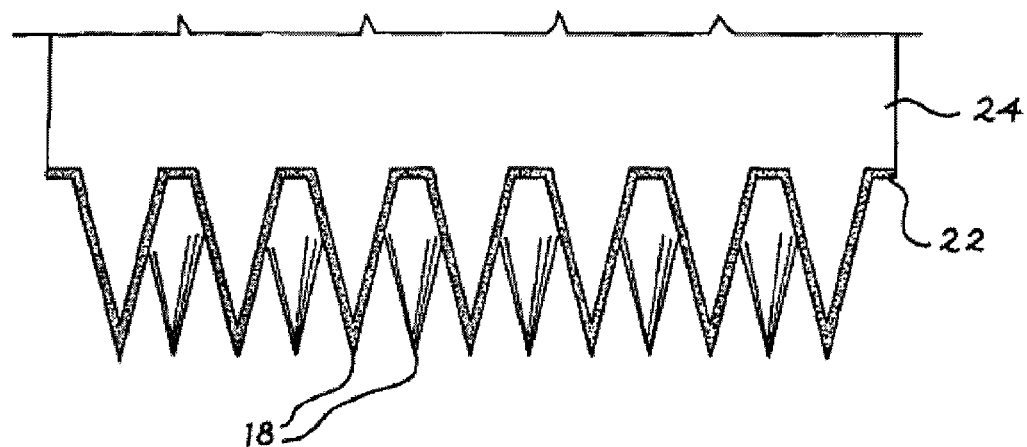
Figure 2C:
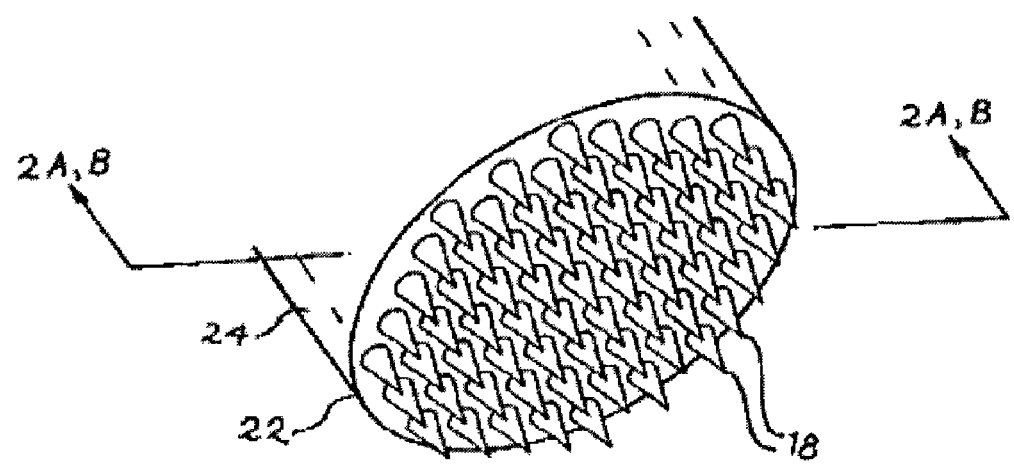

According to one embodiment of the present disclosure, a method is provided for making large area substrates for surface enhanced Raman spectroscopy using a glass-drawing technique. Referring to FIG. 1, a bundle of tubes 1 is formed from a plurality of single dielectric tubes, such as glass tubes. The bundle of glass tubes 1 is drawn, and redrawn if needed, to form a plurality of drawn glass nanotubes 2. The drawn glass nanotubes 2 are cut to form cut drawn nanotubes 3. The cut drawn nanotubes 3 can have any shape in the longitudinal direction of the nanotubes, such as plates, tiles, or disks, based on the pattern the tubes are cut. In one example, the drawn glass nanotubes 2 are cut into disks 3. The cut drawn nanotubes 3 can be etched to form large area substrates with periodicity. In one example, referring to FIGS. 2 and 6, the large area substrates 24 with periodicity comprise an array of sharp surface features 18, as described in detail below. In another example, referring to FIG. 7, the large area substrates 24 with periodicity comprise an array of etched wires and guided light cones. The bundling, drawing, cutting, and etching processes will be described in detail below.

The large area substrates prepared from the structured glass-drawn materials have specific periodicities, coatings, and aspect ratios that may greatly enhance the detection of specific molecules. The particular periodicities (from a few microns to tens of nanometers), coatings (the periodic arrays will typically be coated with a metal such as gold or silver), and aspect ratios fabricated can be optimized based on the particular molecules to be detected. A series of customized arrays that can individually detect specific molecules and collectively characterize a particular chemical and biological environment can be prepared using the glass drawing, bundling, fusion, and etching process.

Any suitable dielectric tubes can be used to prepare the large area substrates. For example, the dielectric tubes can be composite glass rods. The glass rod comprises a matrix material of the rod and a core disposed inside of the matrix material of the rod. The drawn glass nanotubes 2 can assume any shape in the transverse direction of the nanotubes, such as a circle, a square, a rectangle, an oval, a triangle, a hexagonal shape, or an irregular shape. The thickness of the large area substrate 3 in the longitudinal direction may vary according to the applications the substrate will be used for.

The scattering surface of the large area substrates, such as the interface of the recessive and protrusive phase materials shown in FIG. 5B, can be coated with a metal at the interface. Any suitable coating method can be used. In one embodiment, recessive glass tubes into which soft metal coated protrusive glass rods have been placed are drawn. The soft metal can be a single metal such as gold, or a metal composite, such as gold or gold-silver composite. The soft (low melting point) metal will tend to melt as the glasses soften. As the glasses get drawn, the molten metal conforms to the interface between the narrowing tube and rod. The recessive glass tubes also coalesce into the support structure. As the glasses cool and harden so will the metal forming the coating surface around the narrowed protrusive rod. The metal coating may be continuous or discontinuous. Combined with bundling, fusing, wafer cutting, and etching, large area substrates with metal coating can thus be prepared.

In another embodiment, a metal coated protruding phase is formed by using glass rod coated with a metal having a high melting point (such as platinum and tungsten). These metal coated glass rods can be inserted through the core of recessive glass tubes. The recessive glass tubes can then be drawn such that the respective tube coalesces around the metal coated rod without the metal melting or softening as the tube is drawn. Subsequent cutting, bundling, and fusing, as described above, can be used to create large area substrates with metal coating.

The metal can then be etched along with the recessive and protrusive glasses, if needed. Depending on the relative rates of etching, various recessed or protruding metal features can result. By proper choice of the etchant or mixture of etchants a desired structure can be formed at the large area substrates. By use of a metal or other reflective material at the interface of the protrusive phase and the recessive phase support structure, the protrusive phase can have a refractive index that is greater than, equal to, or less than the recessive phase.

In yet another embodiment, a metallic large area structure can be produced by evaporating a thin layer of a metal such as silver, gold, aluminum, or other suitable metals onto the cut drawn nanotubes prepared by the glass drawing technique. The thickness of the metal layer can be less than about 10 nm. At lower thickness, the metal layer may form nanoparticles on the substrate in the form of isolated metal islands. Upon increase of the deposited metal thickness, the coated metal may form a continuous film. Preferably, the thickness of the metal layer is small in order to increase the roughness of the substrate, and thus increase the SERS enhancement effect. The size and shape of the metal nanoparticles can be influenced by varying the thickness of metal deposited and/or by using various coating techniques known to persons with ordinary skill in the art.

The metal coated large area substrates comprise a periodic array of surface features 18. The metallic coating allows binding of analyte molecules to the substrates. The surface features may be substantially uniform in size and shape. The thickness of the metallic coating can be in any predetermined thickness, such as about 10 to 1,000 nm. Preferably, the thickness of the metallic coating is about 50 to 100 nm. The surface features can be in any predetermined size, depending upon the drawing ratio used in the glass drawing process and the etching process used, such as in the size of about 10 to 1,000 nm range. Preferably, the surface features are in the size of about 50 to 200 nm.

The periodicity of the large area substrates can vary, and depends on the diameters of the drawn tubes and the etching process. For example, the shape of the glass tubes can vary. Preferably, the glass tubes are cylindrical. The shape of the bundled drawn glass tubes before cutting can vary. The bundled drawn glass tubes can be a circle, a square, a rectangle, an oval, a triangle, a hexagonal shape, or any predetermined shape. The shape of the surface features on the substrate can vary. For example, the various etching systems, etching time, and differential etchability of the core and matrix material of the glass rod, may each affect the shape of the formed surface features.

The metal coating process may affect the periodicity, depending upon the thickness of the metallic coating. Periodicity refers to the substantially uniform alignment of the surface features on the large areas substrates. The surface feature-to-surface feature spacing can be from a few microns to tens of nanometers. In one example, a regular periodic surface feature-to-surface feature spacing is less than the wavelength of the light used in a spectroscopy application. In another example, a regular periodic surface feature-to-surface feature spacing is about 20 nm or less, including direct particle-to-particle contact. The surface features may have high symmetry or reduced symmetry shape, and more generally may be spherical, spheroid, rod like, cylindrical, nanowire, tubes, toroid, or any other shapes that, when uniform, can be arranged with substantially regular periodicity.

The large area substrate may have a planar or curved shape, as described in co-pending U.S. patent application Ser. No. 12/558,101 to Ivanov et al., filed on the same date as this disclosure, entitled "Method Of Making Large Area Conformable Shape Structures For Detector/Sensor Applications Using Glass Drawing Technique And Postprocessing" and commonly owned by the assignee of the present disclosure, the entirety of which is hereby incorporated by reference.

Parameters, such as the shape and size of the surface features, the spacing between the surface features, and periodicity of the surface features, the dielectric constant and thickness of the dielectric glass substrate, the type and thickness of the metal coating layer, can be optimized for maximum SERS signals for a particular analyte to be analyzed. For example, one of these parameters, such as the size of the surface features, can be varied for optimal enhancement for a particular analyte of interest. In another example, the effect of the metal layer thickness upon SERS enhancement can be optimized. In yet another example, silver-coated substrates may provide strongly enhancing substrates.

The large area substrates can be used to detect a variety of analytes, such as biological or environmental contaminants or other chemical constituents. In one embodiment, the large area substrates can be used as SERS substrates. The analytes can be immobilized to the large area substrates by any suitable method, either physically or chemically. In one example, the metal coated large area substrates are modified to facilitate analyte absorption and thereby bring the molecules as close as possible to the surface of the SERS active particles on SERS probes.

Any suitable immobilization method can be used. In one embodiment, an analyte is immobilized to the large area substrate by physical adsorption. In another embodiment, an analyte is covalently bound to the metal coated large area substrate. In one embodiment, a first biomolecule (a binding agent, such as a polypeptide, an antibody, an antigen, a chemical group, a DNA sequence, a carbohydrate, a bacterium, a pathogen, or a lipid) is immobilized to the metal coated large area substrate using standard coupling methods, such as biologically, physically, or chemically.

For example, a self-assembled monolayer presenting a particular functional group can be formed on the gold-coated large area substrate, and the binding agent is coupled to the functional group on the self-assembled monolayer. A second biomolecule (an analyte of interest, such as an antigen, a virus, a DNA sequence, or a viral or bacterial polypeptide) is bound to the binding agent.

Any suitable coupling method can be used to bind an analyte to the binding agent on the metal-coated, such as gold-coated, large area substrates. For example, when the analyte has a hydroxyl group, it can be coupled to the binding agent using standard coupling chemistry. Alternatively, when the analyte has a maleimidyl or an alpha-halo-amide group, it can be coupled to the binding agent which contains a thiol group (such as Cys), forming a thioether linkage. Alternatively, when the analyte comprises an antibody, it can be coupled to the binding agent which is an antigen. Alternatively, when the analyte comprises an antigen, it can be coupled to the binding agent which is an antibody. Alternatively, when the analyte has an amine group, it can be coupled to the binding agent which contains a carboxylic acid, forming an amide linkage. Alternatively, when the analyte has a thiol group, it can be coupled to the binding agent which contains a thiol group (such as Cys), forming a disulfide linkage. Alternatively, when the analyte has a carboxylic acid, it can be coupled to the binding agent which contains an amine. Alternatively, when the analyte has an aldehyde, it can be coupled to the binding agent which contains amine via reductive amination. Alternatively, when the analyte is a DNA sequence, it can be coupled to the binding agent which has a DNA sequence complimentary to the analyte DNA sequence. Preferably, the analyte is covalently coated to the surface. Other surfaces and coating methods are described in U.S. patent application Publication No. 2007-0048249, published Mar. 1, 2007, the entirety of which is incorporated herein by reference.

In one embodiment, the metal-coated large area substrate in combination with the binding agent has a first measurable SERS signal. The metal-coated large area substrate in combination with both the binding agent and the analyte of interest has a second measurable SERS signal that is different from the first measurable SERS signal. Association of the binding agent with the analyte of interest can be detected because the SERS spectrum of the substrate in combination with the binding agent is detectably different from the SERS spectrum of the substrate in combination with both the binding agent and the analyte of interest.

In another embodiment, the analyte of interest binds directly to the metal-coated large area substrate. For example, a particular biomolecule of interest can be detected because the individual biomolecule of interest have a unique SERS spectrum that is detectably different, and thus distinguishable, from the SERS spectra of other biomolecules. The SERS signal of the metal-coated large area substrate in combination with the analyte of interest is measured. Association of the analyte of interest with the substrate is detected because of the uniqueness of the SERS spectrum of the SERS signal of the metal-coated large area substrate in combination with the analyte of interest.

In yet another embodiment, a set of metal-coated substrates, each customized for a particular analyte of interest, can be prepared. Each substrate may have a different periodicity. The respective analyte of interest is immobilized to the respective substrate. The specificity of analyte detection based on the custom array structures may allow for a set of these structures to be used simultaneously to detect specific pathogens and other biological components.

Figure 3A:
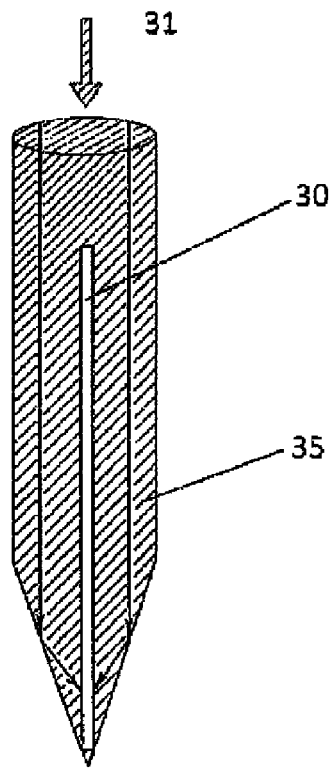
FIG. 3 is a not-to-scale schematic view of a single etched wire and an array of etched wires on large area substrates for surface enhanced Raman spectroscopy.
Figure 3B:
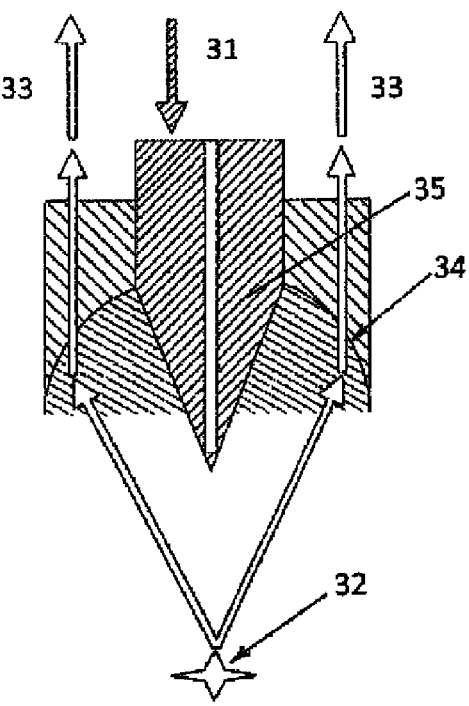
Figure 3C:
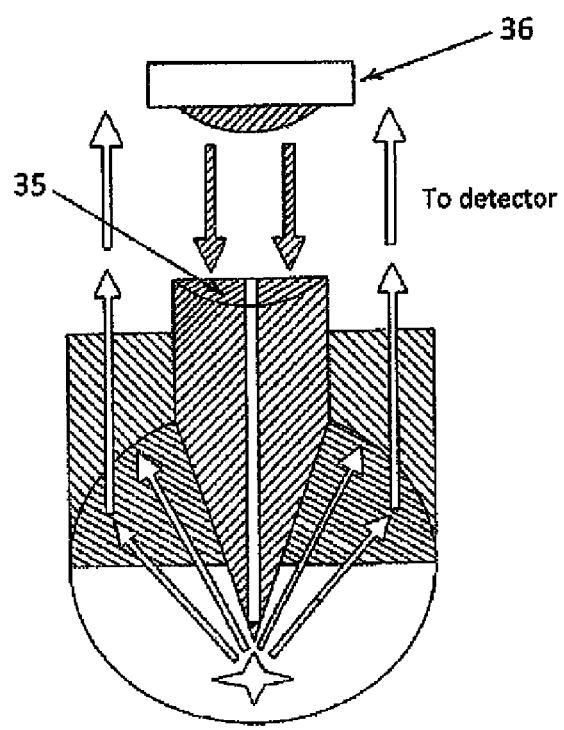
Figure 3D:
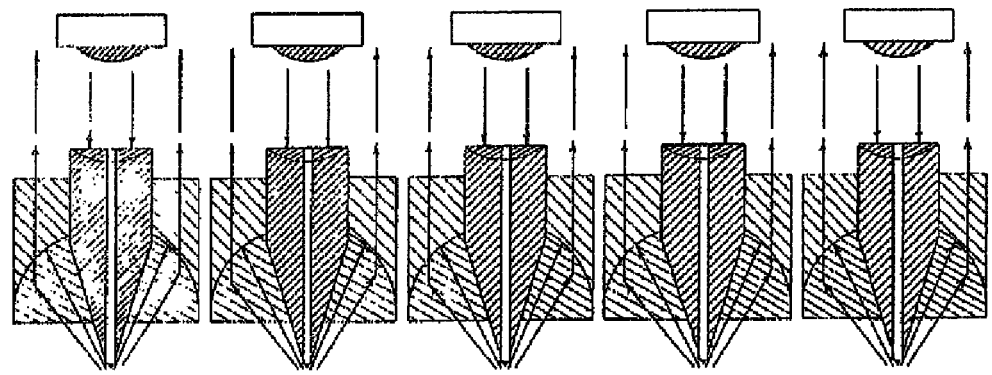

Referring to FIG. 3A, a fiber 35 with an Au wire 30 is prepared. The Au wire 30 has a diameter of less than about 1 micron (condition of SERS). Laser 31 (Raman excitation) is focused and coupled to the Au wire 30 producing a surface plasmon. Referring to FIG. 3B ad 3C, Raman scattering occurs when the laser 31 is scattered from the Raman scattering object 32. The etched surface 34 couples the Raman scattered light 33 back to the fiber 35 and the detector 36. Etched fiber 35 may collimate excitation light into excitation fiber. In one example, the excitation source (laser/LED 31) is directly coupled to the fiber 35, forming an elemental "pixel" of Raman scattering multi-pixel assembly. Referring to FIG.

Figure 3E:
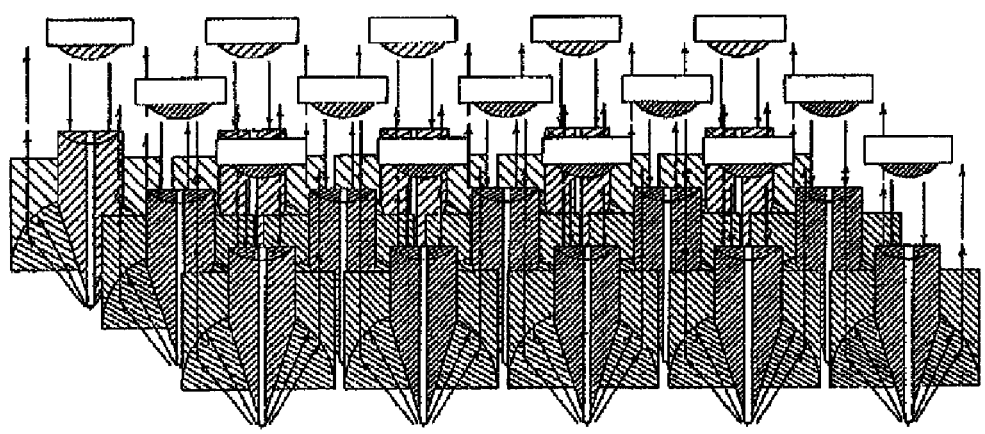

3D, a design of a 5-pixel array is shown. At each position, 5 areas of sample areas can be probed and surface enhanced Raman spectra can be acquired. Mapping of the sample could be obtained by shifting the matrix in the x-y-z plane. Referring to FIG. 3E, a design of a 5×3 pixel matrix is shown. At each position, 15 areas of sample areas can be probed and surface enhanced Raman spectra can be acquired. Mapping of the sample could be obtained by shifting the matrix in the x-y-z plane.

Glass Drawing Techniques

The nanotubes for substrates assembly can be prepared by any suitable method, for example, by etching, chemical or physical vapor deposition, laser vaporization, electrical field manipulation, hydrodynamic flow, lithographic techniques, synthetic methods, and glass drawing techniques. Preferably, the nanotubes are prepared by glass drawing techniques.

Figure 4:
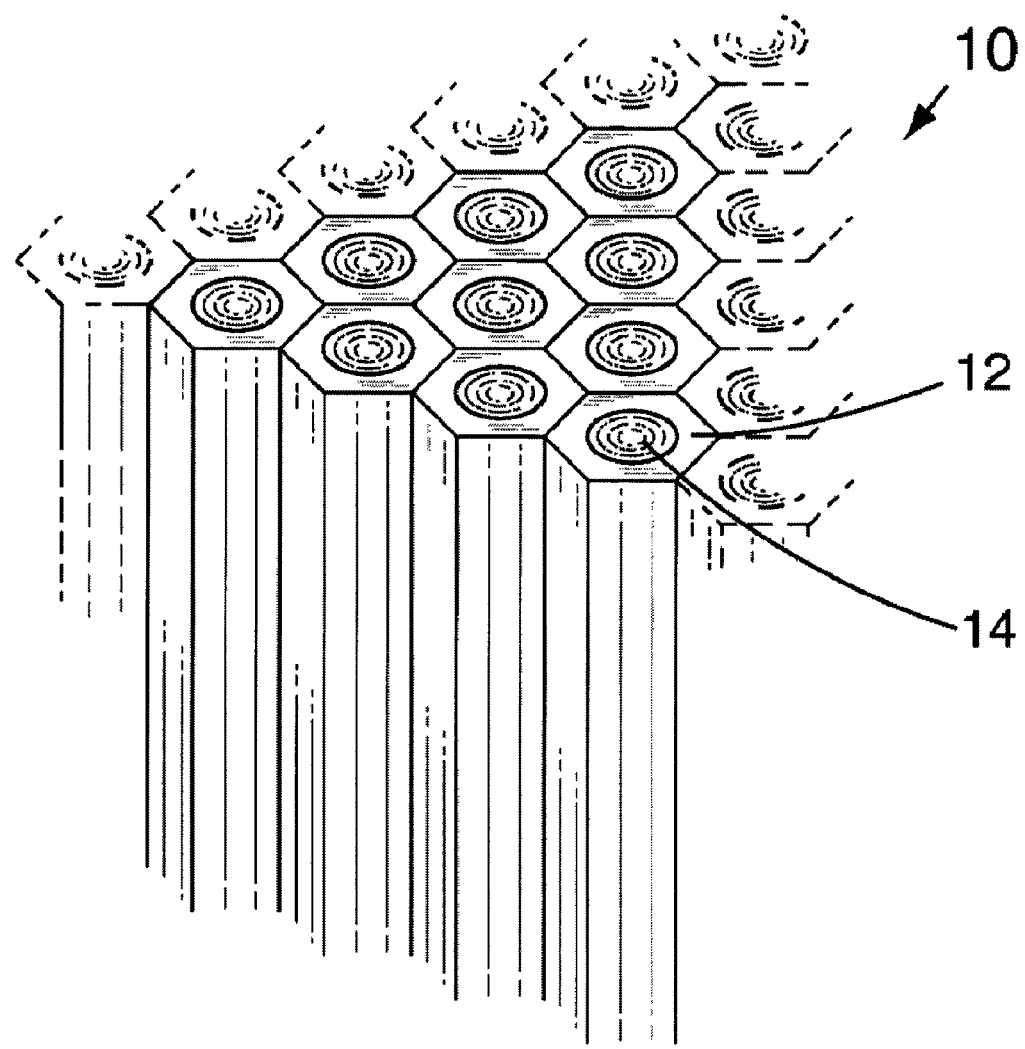
FIG. 4 is a schematic oblique view of a portion of a bundle of composite rods.

In one embodiment, composite glass rods are drawn. Referring to FIG. 4, composite rods comprise a core 14 and a sleeve (the matrix material of the rods) 12. The core 14 comprises a different material than the matrix material 12. The composite rods are bundled in an aligned array, or bundle 10. The rod (matrix material) 12 and the core 14 can assume any shape. Preferably, the rod (matrix material) 12 has a hexagonal or other outer cross-sectional shape to minimize voids while the core 14 preferably has a circular cross-section, although neither of these parameters is considered to be critical. It may be advantageous for economical manufacturing for the matrix material 12 to have a circular cross-section. In this case the voids are filled in during subsequent processing. With round rods 12, the spacing of the core 14 will be somewhat less precise.

The matrix material 12 and core 14 are preferably selected based on differential etchability (susceptibility to etching or dissolution). In the case of the nano-channel glass drawing, the core glass has a much higher etchability than that of the matrix glass. Alternatively, if the core 14 has a lower etchability than the matrix material 12, protrusive, sharp features, such as nanocones and nanospikes, may form upon etching of the composite surface.

It should be noted that the use of immiscible components in the composite may improve the ease of drawing the material. In general it may be advantageous to choose materials with specific miscibility to facilitate drawing without too much inter-diffusion of the materials (excessively miscible) and without either component breaking up into droplets (insufficiently miscible).

The bundle 10 can heated to a temperature sufficient to soften the materials comprising the bundle 10, but low enough to avoid damage, decomposition, or other deleterious changes. The bundle 10 is then drawn along the axis of the bundled rods to fuse and reduce the diameter of the bundle 10. The drawn bundle has reduced size material rod matrix material 12 and respective core 14. The drawn bundle is cut transversely into sections which can be re-bundled to increase the number of core material cores in the cross-section thereof.

The drawn bundle can then be drawn again. The twice-drawn bundle has further reduced size material rod matrix material 12 and respective core 14. The twice-drawn bundle is again cut transversely into sections which are re-bundled to further increase the number of core 14 cores in the cross-section thereof.

The process of bundling, drawing, and cutting can be performed a single time or repeated many times until the desired diameter and spacing of the core 14 are obtained. Core 14 diameters and spacing on the nanometer scale are possible. The sizes of bundles and the number of rods contained therein can be varied throughout the process as desired.

Figure 5:
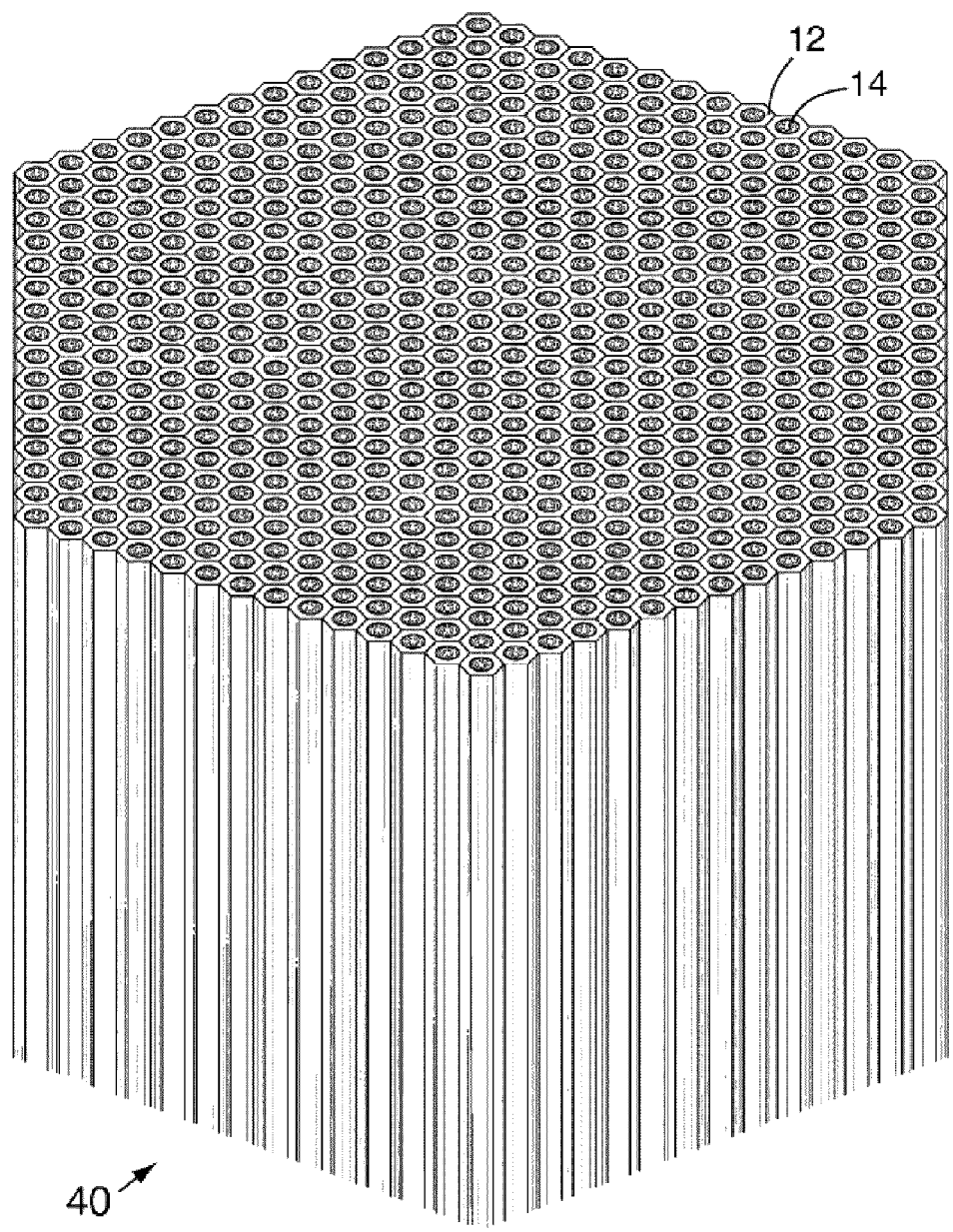
FIG. 5 is a schematic oblique view of the bundle of composite rods shown in FIG. 3 after re-bundling and fusing.

After the final draw (which can be the first draw), the bundle can be cut, bundled, and fused in order to obtain a larger diameter boule. Referring to FIG. 5, the boule 40 can be transversely cut to produce slices (plates, tiles) of any desired thickness. The cut is usually (but not necessarily) perpendicular to the original rods 12 and the drawing direction. One or both cut faces may be polished. Although a hexagonal boule 40 is shown and described as an example, a boule of any desired geometric shape can be formed, processed, and used.

In another embodiment, the composite material may comprise a bundle of more than one kind of composite rod, as described in U.S. Patent Publication No. 2006/0289380, the entirety of which is hereby incorporated by reference. For example, some of the cores may have a different core phase having a high etchability/solubility (e.g., nano-channel-like cores) so that a perforated product may be fabricated.

In yet another embodiment, solid glass rods or hollow glass tubes are used as opposed to composite glass rods. The process of bundling, drawing, and cutting is otherwise performed as described above.

In further another embodiment, glass tubes that contain appropriate filling materials in powder or rod form are drawn. The drawing method according to the embodiment combines fiber drawing method with advanced filling materials, thus providing not only desired functionality, but also excellent controls over the aspect ratio, diameter, length and inter-nanotube spacing of micro/nanotubes.

A preform for drawing may be prepared by pouring powders or inserting a rod into a glass tube. Drawn tubes from the first drawing process are cut into pieces, preferably with substantially equal length, which are bundled together to form a hexagonal bundle for the next drawing cycle. By repeating the drawing-cutting-bundling process for as many, or as few, times as needed, the outer and the inner diameters, and the thickness of the glass tubes may be decreased from centimeters to hundreds nanometers or less.

After the last drawing, the drawn nanotubes are bundled and annealed below the softening temperature of the glass to make a solid rod. In one example, the rod is cut perpendicular to its axis to make plates that have ordered array of micro/nanotubes of the filling materials. If needed, after making encapsulated nanotubes, the glass can be removed by etching, such as hydrogen fluoride etching. The nanotubes prepared can have a nanometer size diameter, and a length of several meters or longer. Preferably, a vacuum pump is connected to the glass tube, and the drawing is done in vacuum to avoid the possible oxidation of the filling materials and to make an intimate contact between the glass and the filling materials.

Any suitable material can be used as the filling material in the preform. Preferably, the softening temperature of the glass is between the melting temperature and the boiling temperatures of the filling material. Preferably, the coefficients of thermal expansion of the glass and the filling material at the drawing temperature are close to each other, or the filling material is in liquid. Preferably, there is substantially no chemical reaction between the glass and the material at the drawing temperature. Preferably, the molten material has certain wettability to the glass surface. Preferably, the materials do not have high vapor pressure at high temperature.

The drawn nanotubes can be etched and/or coated using any suitable methods. For example, the drawn nanotubes can be etched and coated as described in U.S. Patent Publication No. 2006/0289380, the entirety of which is hereby incorporated by reference.

Structured Substrates

The cut drawn nanotubes prepared by the glass drawing technique can be used to fabricate structured substrates, such as nanotubes with protrusive spikes. In one embodiment, composite rods comprising a core 14 and a sleeve (the matrix material of the rods) 12 are drawn as described above. The matrix material of the rods 12 and the core 14 comprises a recessive phase material and a protrusive phase material, respectively. The respective phases provide differential etchability. In one example, the recessive phase has a greater etchability than the protrusive phase.

Figure 6A:
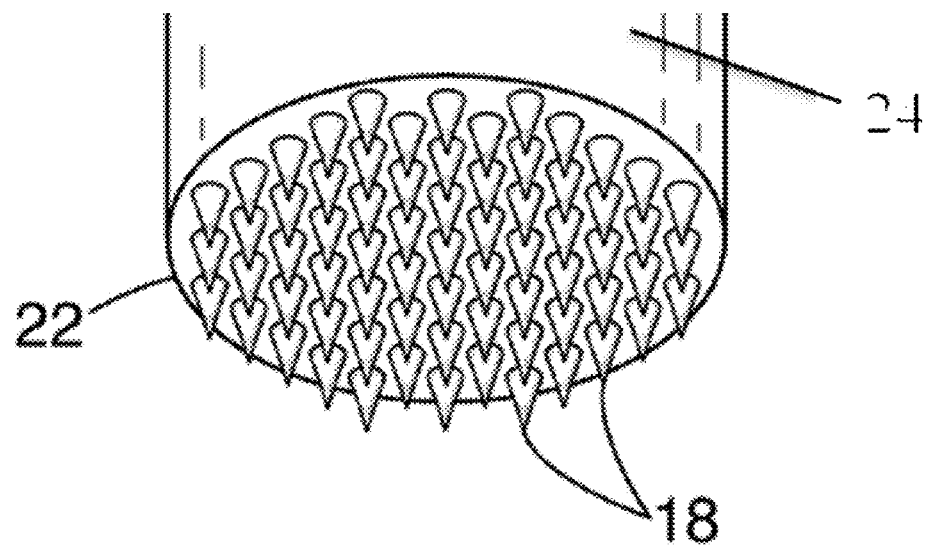
FIG. 6A is a not-to-scale schematic illustration of a structured substrate with protrusive phases.
Figure 6B:
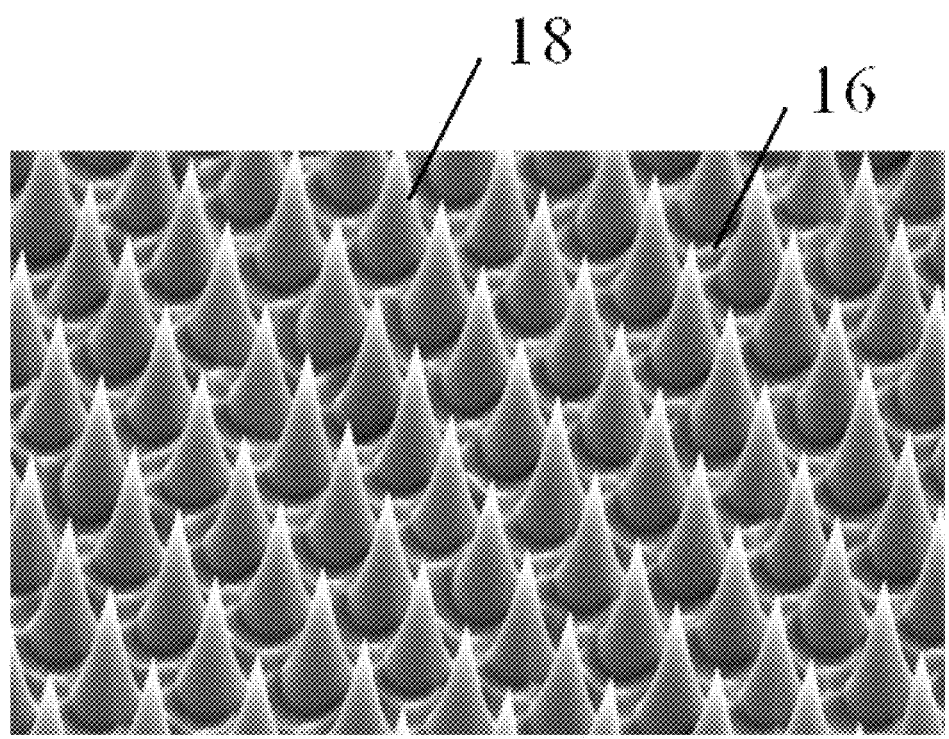
FIG. 6B and 6C are oblique photomicrographs of an spiked glass plate such as that shown in FIG. 5A after etching.
Figure 6C:
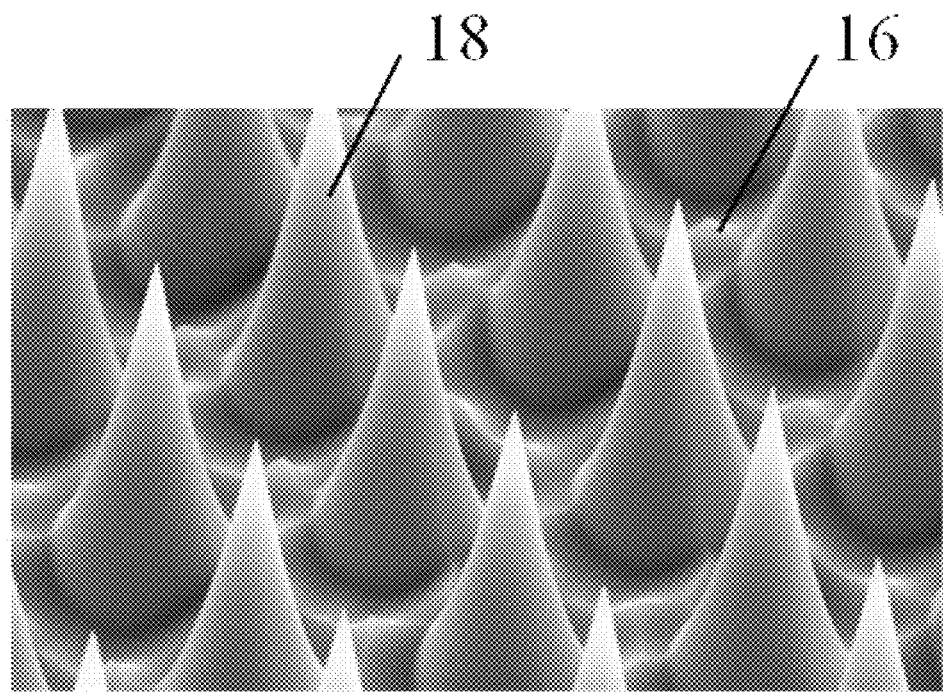
Figure 7A:
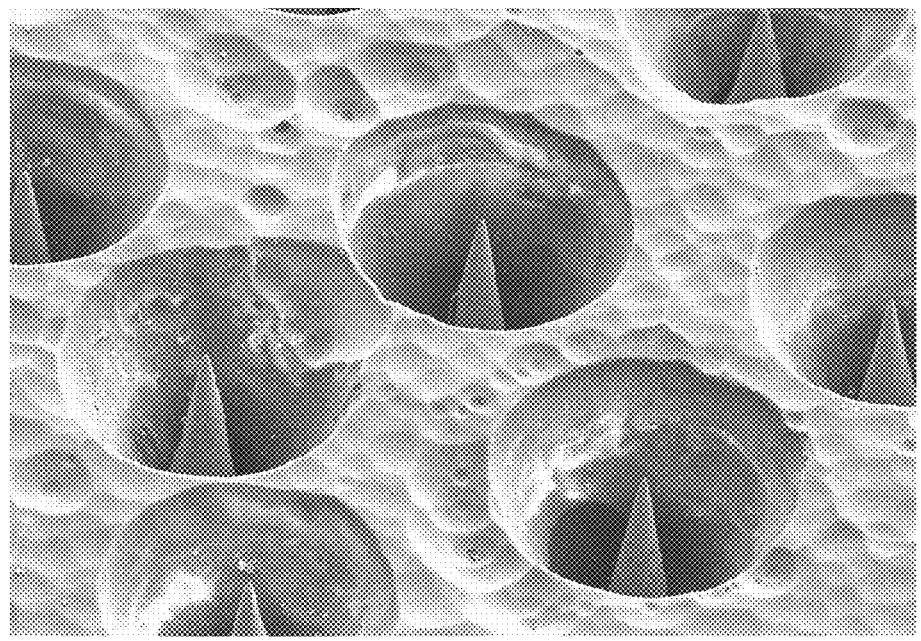
FIG. 7A and 7B are oblique photomicrographs of an etched wire array and guided light cone array.
Figure 7B:
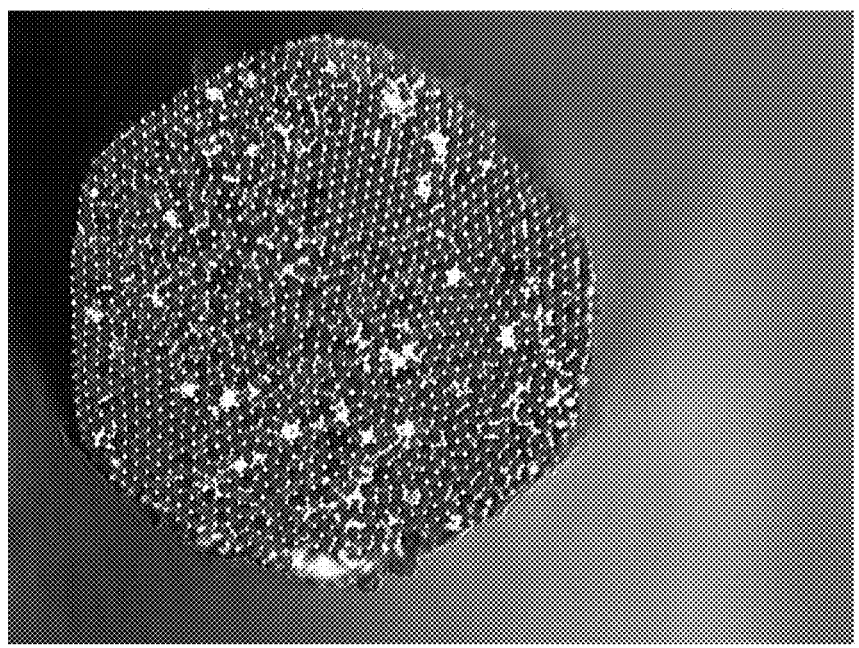

Referring to FIG. 6, by subjecting the surface of the composite structure to an etchant that removes more of the recessive phase 16 than the protrusive phase, the portion of the protrusive phase exposed to the etchant forms sharp, protruding surface features 18 on the surface 22 of the composite structure to form the structured substrate 24. The structured substrate 24 comprises an array of sharp surface feature tips or spikes 18. Such an array can have from as few as two to more than one billion per square centimeter of individual, parallel sharp points that form a pre-determined periodicity on the substrate. The protrusive phase 18 is generally surrounded by the recessive phase 16 in regions adjacent to the tips or spikes 18.

The phrase "sharp surface feature" is defined to mean a generally tapered, protrusive structure that preferably terminates in a sharp terminus, ideally an atomically sharp point or ridge. "Sharp surface feature" can therefore refer to a feature having a base portion having a first cross sectional area, and a tip portion opposite the base portion having a reduced cross sectional area that is no more than 30% of the first cross sectional area, such as 25%, 20%, 15%, 10%, 8%, 6%, 5%, 4%, 3%, 2%, 1%, or less than 1% of the first cross sectional area. The reduction in cross sectional area in traversing from the base portion to the tip portion is preferably monotonic.

Sharp surface features include, but are not limited to, protrusions such as spikes and/or ridges. The protrusive phase is sharpened because the protrusive phase etches in the process, but at a slower rate than the recessive phase and because the distal tip is exposed for a greater period of time than the base portion as the recessive phase must be removed before significant surface area of the protrusive phase can be etched. The use of any differentially etchable recessive and protrusive materials in any combination to produce the desired effect is considered to fall within the scope of the present disclosure. Moreover, there are no limits to the variations of sizes and shapes of the sharp surface features. The composite base material may be made from any materials differentially etchable by any known etching method or methods.

The composite base material may be made from any materials which have suitable differential etching characteristics. Suitable materials include, for example, glasses, metals (including alloys), ceramics, polymers, resins, and the like. Choices of materials can have an effect on properties of the product, such as, for example, chemical resistance, ease and/or need of coating, strength, toughness, flexibility, elasticity, and plasticity.

Any suitable etching system can be used. In one example, the etchant comprises an organic or inorganic acid or alkali; polar, nonpolar, organic, inorganic, or mixed solvent; or mixtures of any of the foregoing. The etchant is selected to etch the composite material differentially as described herein. For example, an aqueous acid such as HF, HCl, HBr, or HI might be selected to etch glass compositions differentially.

The etchant can be a "mixed etchant system" which is comprised of a plurality of etchants that give different etch contrast ratios when applied to the composite surface. For example, one etchant can preferentially etch one phase while the other etchant can preferentially etch the other phase. A mixed etchant system can be particularly useful because the contrast ratio of the etching process can be modified by changing the composition and/or relative concentrations of the etchants. An example of a mixed etchant system is a mixture of HF and HCl. The possible compositions of suitable mixed etchant systems are substantially without limits.

Any suitable etching method can be used, as long as the desired surface feature is achieved. For example, other, non-solution etching techniques may be used, such as plasma etching or other isotropic etch techniques. The etching continues until the recessive matrix material is etched back to the desired depth, leaving some of the core material protruding from the surface. The result is that the etched core material is sharpened to a cone-shaped spike, the aspect ratio of the spike being dependent on the ratio of the matrix material and core material etching rates.

The structured substrates can be either super-hydrophobic or super-hydrophilic by coating the protrusive features with an appropriate material, as described in U.S. Pat. Pub. No. 2006/0289380; U.S. Pat. No. 2008/0080816; U.S. Pat. No. 7,258,731; U.S. Pat. Pub. No. 2009/0042469; and U.S. Pat. No. 7,150,904, the entireties of all of which are hereby incorporated by reference.

While the present disclosure has been described with reference to certain embodiments, other features may be included without departing from the spirit and scope of the present invention. It is therefore intended that the foregoing detailed description be regarded as illustrative rather than limiting, and that it be understood that it is the following claims, including all equivalents, that are intended to define the spirit and scope of this invention.

The invention claimed is:

1. A method of making an array of large area substrates, comprising:
    drawing a plurality of tubes to form a plurality of drawn tubes;
    cutting the plurality of drawn tubes into cut drawn tubes, each cut drawn tube having a first end and a second end along the longitudinal direction of the respective cut drawn tube, the cut drawn tubes collectively having a first predetermined periodicity;
    forming a plurality of surface features on the first ends of the plurality of cut drawn tubes;
    forming a first metal layer on the first ends of the cut drawn tubes to provide a first large area substrate, the plurality of surface features on the first ends having a first aspect ratio;
    repeating the above steps to provide a second large area substrate having a second predetermined periodicity, a second metal layer on the first ends of the cut drawn tubes, and a plurality of surface features on the first ends of the cut drawn tubes having a second aspect ratio, at least one of the second predetermined periodicity, the second metal layer and the second aspect ratio of the second large area substrate being different from the respective first predetermined periodicity, first metal layer and first aspect ratio of the first large area substrate; and
    bundling the first and second large area substrates to provide an array of large area substrates.

2. The method of claim 1, wherein forming the plurality of surface features comprises etching the first ends of the plurality of cut drawn tubes.

3. The method of claim 2, wherein the tubes are composite glass tubes each comprising a glass rod and a core disposed inside of the glass rod, wherein the glass rod has an etchability different from that of the core.

4. The method of claim 1, wherein the size of the plurality of surface features is sufficient such that each large area substrate with the plurality of surface features is adapted for surface enhanced Raman spectroscopy.

5. The method of claim 1, wherein forming each metal layer comprises coating the first end of the cut drawn tubes with a metal.

6. The method of claim 1, further comprising:
bundling the plurality of tubes before drawing.

7. The method of claim 6, wherein the bundling, drawing, and cutting steps are repeated at least once during the formation of each large area substrate.

8. The method of claim 1, wherein each metal layer comprises a metal selected from a group consisting of gold, silver, aluminum, and combinations thereof.

9. The method of claim 8, wherein each metal is gold.

10. The method of claim 1, wherein each metal layer is discontinuous.

11. The method of claim 10, wherein each metal layer comprises metal nanoparticles.

12. An array of large area substrates, comprising:
a first large area substrate comprising a plurality of bundled drawn tubes each having a first end and a second end along the longitudinal direction of the bundled drawn tubes, the bundled drawn tubes collectively having a first predetermined periodicity, the first ends of the plurality of bundled drawn tubes having a plurality of protrusive surface features, the protrusive surface features having a first aspect ratio; and a first metal layer disposed on the plurality of protrusive surface features; and
a second large area substrate comprising a plurality of bundled drawn tubes each having a first end and a second end along the longitudinal direction of the bundled drawn tubes, the bundled drawn tubes collectively having a second predetermined periodicity, the first ends of the plurality of bundled drawn tubes having a plurality of protrusive surface features, the protrusive surface features having a second aspect ratio; and a second metal layer disposed on the plurality of protrusive surface features,
the first and second large area substrates being bundled together, at least one of the second predetermined periodicity, the second metal layer and the second aspect ratio of the second large area substrate being different from the respective first predetermined periodicity, first metal layer and first aspect ratio of the first large area substrate.

13. The array of claim 12, wherein the size of the plurality of protrusive surface features is sufficient such that each large area substrate with the plurality of protrusive surface features is adapted for surface enhanced Raman spectroscopy.

14. The array of claim 12, wherein the thickness of each metal layer is about 10 nm or less.

15. The array of claim 12, wherein the protrusive surface features are substantially uniform in size and shape.

16. The array of claim 12, wherein each metal layer comprises a metal selected from a group consisting of gold, silver, aluminum, and combinations thereof.

17. The array of claim 16, wherein each metal is gold.

18. The array of claim 12, wherein each metal layer comprises metal nanoparticles.

19. A method for detecting a plurality of analytes, comprising:
providing an array of large area substrates, the array comprising
a first large area substrate comprising a plurality of bundled drawn tubes each having a first end and a second end along the longitudinal direction of the bundled drawn tubes, the bundled drawn tubes collectively having a first predetermined periodicity, the first ends of the plurality of bundled drawn tubes having a plurality of protrusive surface features, the protrusive surface features having a first aspect ratio; and a first metal layer disposed on the plurality of protrusive surface features; and
a second large area substrate comprising a plurality of bundled drawn tubes each having a first end and a second end along the longitudinal direction of the bundled drawn tubes, the bundled drawn tubes collectively having a second predetermined periodicity, the first ends of the plurality of bundled drawn tubes having a plurality of protrusive surface features, the protrusive surface features having a second aspect ratio; and a second metal layer disposed on the plurality of protrusive surface features,
the first and second large area substrates being bundled together, at least one of the second predetermined periodicity, the second metal layer and the second aspect ratio of the second large area substrate being different from the respective first predetermined periodicity, first metal layer and first aspect ratio of the first large area substrate; and
contacting the array of large area substrates with a plurality of analytes.

20. The method of claim 19, wherein each large area substrate is customized to detect one of the plurality of analytes.

* * * * *